(12) United States Patent
Elfström et al.

(10) Patent No.: US 9,408,757 B2
(45) Date of Patent: Aug. 9, 2016

(54) TOOL FOR ANALYSING LIQUID DISCHARGE DATA IN AN ABSORBENT ARTICLE, AN ABSORBENT ARTICLE ADAPTED FOR LIQUID DISCHARGE DATA COLLECTION AND A CONTROL UNIT INTERACTING WITH THE ABSORBENT ARTICLE FOR COLLECTING THE LIQUID DISCHARGE DATA

(75) Inventors: Allan Elfström, Philadelphia, PA (US); Mattias Bosaeus, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 199 days.

(21) Appl. No.: 13/996,896

(22) PCT Filed: Dec. 20, 2011

(86) PCT No.: PCT/EP2011/073456
§ 371 (c)(1),
(2), (4) Date: Aug. 1, 2013

(87) PCT Pub. No.: WO2012/084987
PCT Pub. Date: Jun. 28, 2012

(65) Prior Publication Data
US 2013/0303867 A1 Nov. 14, 2013

(30) Foreign Application Priority Data
Dec. 23, 2010 (GB) .................................. 1022028.3

(51) Int. Cl.
*A61F 13/42* (2006.01)
*A61F 13/15* (2006.01)

(52) U.S. Cl.
CPC ....... *A61F 13/42* (2013.01); *A61F 2013/15154* (2013.01); *A61F 2013/424* (2013.01)

(58) Field of Classification Search
CPC ........... A61F 13/42; A61F 2013/15154; A61F 2013/424; A61B 5/202; A61B 5/207; A61B 5/208

USPC .............. 604/361; 600/584; 340/573.5, 604
See application file for complete search history.

(56) References Cited

U.S. PATENT DOCUMENTS

| 5,537,095 A | 7/1996 | Dick et al. |
| 5,808,554 A | 9/1998 | Shuminov |

(Continued)

FOREIGN PATENT DOCUMENTS

| AU | 63393/94 A | 12/1994 |
| EP | 1356798 A1 | 10/2003 |

(Continued)

OTHER PUBLICATIONS

International Preliminary Report on Patentability (IPRP) dated May 21, 2013 that issued in corresponding international application No. PCT/EP2011/073456 filed Dec. 20, 2011 (11 pages).

(Continued)

*Primary Examiner* — Lynne Anderson
(74) *Attorney, Agent, or Firm* — Drinker Biddle & Reath LLP (57) ABSTRACT

An absorbent article for absorbing liquid discharge when worn on the crotch region of the body of a user includes a plurality of detection zones for detecting the liquid discharge. Each detection zone is provided by first and second electrically conductive paths that are electrically isolated from one another and arranged so that a liquid discharge between the first and second conductive paths allows electrical current to flow between the first and second conductive paths which is able to be detected to detect the presence of liquid discharge in the respective zone. The plurality of zones are longitudinally distributed with respect to the absorbent article along an absorbent core of the absorbent article, to allow the longitudinal extent of the discharge to be ascertained. The first and second conductive paths are longitudinally spaced from one another. The first and second conductive paths are elongate and are laterally aligned.

34 Claims, 2 Drawing Sheets

(56) References Cited

U.S. PATENT DOCUMENTS

| | | | |
|---|---|---|---|
| 6,246,330 | B1 | 6/2001 | Nielsen |
| 7,141,715 | B2* | 11/2006 | Shapira .................... 604/361 |
| 7,250,547 | B1 | 7/2007 | Hofmeister et al. |
| 8,115,643 | B2* | 2/2012 | Wada et al. ................. 340/573.5 |
| 2002/0145526 | A1 | 10/2002 | Friedman et al. |
| 2004/0207530 | A1 | 10/2004 | Nielsen |
| 2005/0156744 | A1* | 7/2005 | Pires ..................... 340/573.5 |
| 2005/0195085 | A1* | 9/2005 | Cretu-Petra ............... 340/573.5 |
| 2006/0061477 | A1* | 3/2006 | Yeh ...................... 340/573.5 |
| 2006/0244614 | A1 | 11/2006 | Long |
| 2007/0142796 | A1 | 6/2007 | Mosbacher et al. |
| 2007/0252713 | A1 | 11/2007 | Rondoni et al. |
| 2007/0270774 | A1 | 11/2007 | Bergman et al. |
| 2008/0094226 | A1 | 4/2008 | O'Shea et al. |
| 2008/0243099 | A1 | 10/2008 | Tippey et al. |
| 2008/0262452 | A1* | 10/2008 | McGinnis et al. ............ 604/359 |
| 2009/0315728 | A1 | 12/2009 | Ales, III et al. |
| 2009/0326417 | A1 | 12/2009 | Ales, III et al. |
| 2009/0326492 | A1 | 12/2009 | Hietpas |
| 2010/0241094 | A1* | 9/2010 | Sherron ..................... 604/361 |
| 2011/0263952 | A1 | 10/2011 | Bergman et al. |
| 2011/0295619 | A1 | 12/2011 | Tough |

FOREIGN PATENT DOCUMENTS

| | | |
|---|---|---|
| EP | 1852067 A2 | 11/2007 |
| EP | 1 903 333 A1 | 3/2008 |
| JP | 2-174846 A | 7/1990 |
| JP | H04-6401 A | 1/1992 |
| JP | 10-151154 A | 6/1998 |
| JP | 2000-325379 A | 11/2000 |
| JP | 2003-111797 A | 4/2003 |
| JP | 2005-32398 A | 2/2005 |
| JP | 2007-296024 A | 11/2007 |
| JP | 2009-505778 A | 2/2009 |
| JP | 2009-519751 A | 5/2009 |
| WO | WO-96/14813 A1 | 5/1996 |
| WO | WO-96/20681 A1 | 7/1996 |
| WO | WO-99/51179 A1 | 10/1999 |
| WO | WO-00/00144 A2 | 1/2000 |
| WO | WO-02/078513 A2 | 10/2002 |
| WO | WO-02/101679 A1 | 12/2002 |
| WO | WO-2004/100763 A2 | 11/2004 |
| WO | WO-2006/047815 A1 | 5/2006 |
| WO | 2007/027258 A1 | 3/2007 |
| WO | 2007/070266 A1 | 6/2007 |
| WO | WO-2007/069945 A1 | 6/2007 |
| WO | WO-2008/147612 A1 | 12/2008 |
| WO | WO-2009/156912 A2 | 12/2009 |
| WO | WO-2010/049827 A2 | 5/2010 |
| WO | WO-2011/054045 A1 | 5/2011 |
| WO | WO-2011/156862 A1 | 12/2011 |

OTHER PUBLICATIONS

English translation of Notice of Reason for Rejection issued Feb. 1, 2016 in Japanese Patent Application No. 2013-545319.

* cited by examiner

Fig. 1

TOOL FOR ANALYSING LIQUID DISCHARGE DATA IN AN ABSORBENT ARTICLE, AN ABSORBENT ARTICLE ADAPTED FOR LIQUID DISCHARGE DATA COLLECTION AND A CONTROL UNIT INTERACTING WITH THE ABSORBENT ARTICLE FOR COLLECTING THE LIQUID DISCHARGE DATA

CROSS-REFERENCE TO PRIOR APPLICATION

This application is a §371 National Stage Application of PCT International Application No. PCT/EP2011/073456 filed Dec. 20, 2011, which claims priority to GB 1022028.3, filed Dec. 23, 2010, both of which are incorporated herein in their entirety.

TECHNICAL FIELD

The present disclosure is concerned with an absorbent article including liquid discharge detection means. Further, the present disclosure concerns a control unit for interrogating the liquid discharge detection means to obtain liquid discharge data for the absorbent article and also to obtain data concerning wearing conditions. Furthermore, the present disclosure is concerned with an analytics tool that utilises the data from the control unit to analyse liquid discharge performance of the absorbent article among other analytic operations.

BACKGROUND

It is known in the art to provide an absorbent article with liquid discharge detection sensors. Such an absorbent article is known from patent publication AU-B -63393/94. The absorbent article of this prior publication has a sensor mounted therein that is able to determine when urination has taken place. The absorbent article is fitted with a transmitter that signals to a nursing station at the occurrence of urination to allow a nurse to take action (i.e. to replace the wet absorbent article with a dry one). The system also allows the time of urination to be recorded in order for urination patterns to be monitored for a given patient.

SUMMARY

The present disclosure aims to provide data that is not only indicative of when an absorbent article has been wetted (i.e. subjected to a liquid discharge), but also to allow an analysis of the performance of the absorbent article in absorbing the liquid discharge, as well as to allow patient diagnostic information to be obtained (such as a type of incontinence that the patient may have). In order to achieve this, the present disclosure offers an improved liquid discharge detection arrangement that enables liquid discharge spread information to be obtained. The present disclosure further offers the recording or otherwise obtaining of more useful data for making an analysis of absorbent article performance and wearer diagnostic information. Furthermore, the present disclosure discloses ways to use the data in making the absorbent article performance or wearer diagnostic analysis.

An absorbent article system according to the disclosure enables determination of the extent and/or location of urination (or perhaps faecal or menstrual matter).

In one aspect, there is provided an absorbent article for absorbing liquid discharge (i.e. urination, menstruation or faecal liquid) when worn in the crotch region of the body of a user, the absorbent article including a plurality of detection zones for detecting the liquid discharge, each detection zone provided by first and second electrically conductive paths that are electrically isolated from one another, and arranged so that a liquid discharge between the first and second conductive paths allows electrical current to flow between the first and second conductive paths, which is able to be detected to detect the presence of liquid discharge in the respective zone. The plurality of zones are longitudinally and/or laterally distributed to allow the longitudinal and/or lateral extent of the discharge to be ascertained. In use, a conductive bridge is formed between the otherwise electrically isolated first and second conductive paths by liquid discharge absorbed in the absorbent core. The liquid detection is doable by measuring a change in electrical property of any electric current that flows between the first and second conductive paths such as conductance, resistance, impedance, capacitance or admittance.

The absorbent article thus has a distribution of isolated conductive paths that allow detection of urination between two of them. One can thus determine the spread of liquid in the absorbent article by activation of a detection zone because the liquid discharge will short circuit two of the conductive paths, which short circuit can be detected. The spread of liquid discharge is indicative of the volume of liquid discharge, which is a useful parameter to know when analysing the absorbency effectiveness of an absorbent article. The longitudinal spread over time of a liquid discharge offers a good indication of separate instances of liquid discharge.

In a particular embodiment, the detection zones are distributed longitudinally with respect to the absorbent article, for the longitudinal extent of a discharge can be equated reasonably well to the volume of discharge as compared to the lateral spread.

In certain embodiments, the first and second conductive paths are longitudinally spaced from one another.

In a particular embodiment, an absorbent article includes a top sheet for allowing the liquid discharge to enter to the absorbent article, a back sheet for preventing the liquid discharge from escaping the absorbent article, and an absorbent core captured between them. The zones are distributed along at least 30% of the longitudinal extent of the absorbent core, at least 40%, at least 50%, at least 60%, at least 70%, or at least 80%. The longitudinal extent of the absorbent core should be understood with respect to the totality of absorbent layers (if there is more than one).

In certain embodiments, the first and second conductive paths are elongated and are laterally aligned.

For an effective discharge volume detection system, there is at least three, four, five, six, seven, eight, nine, ten, eleven, twelve, fifteen, twenty, thirty or even fifty detection zones. The greater the number of zones there are, the more accurate that the liquid discharge spread can be determined. This is to be counterbalanced with the disadvantages of increased quantity of conductive paths, increased numbers of connections to a control unit and increased signal processing requirements of the controller. In a particular embodiment, there are 4 to 12, or more particularly 8 detection zones.

In the context of an absorbent article including a back sheet for preventing the liquid discharge from escaping from the back of the absorbent article and a top sheet for allowing the liquid discharge to enter the absorbent article, and which together capture an absorbent core, the first and second conductive paths extend laterally at least about 50% of the full extent of the absorbent core, at least about 60%, at least about 70%, at least about 80%, or at least about 90%. The lateral extent of the first and second conductive paths means that even off-centre liquid discharges can be reliably determined.

In a certain embodiment, the first and second conductive paths are in conductive contact with a respective conductive section insulated from an absorbent core of the absorbent article, whereby the first and second conductive paths are in electrical contact with the absorbent core. The respective conductive section can be arranged to provide a lead from a control unit contact area of the absorbent article to the respective conductive path. The conductive sections may be insulated from the absorbent core by an insulating layer or by being spaced from the absorbent core. In a certain construction, the conductive sections are arranged on one side of an electrically insulative layer of the absorbent article and the conductive paths are arranged on the other side of the layer to be in electrical contact with the absorbent core. The first and second conductive paths may pass through the insulating layer.

In an embodiment, the control unit contact area is located at a waistband of the absorbent article, in a particular example, as a protruding tab.

Thus, the conductive paths are in continuous electrical contact with the absorbent core, while the leads are insulated therefrom. Apart from the insulative layer, the leads and the conductive paths may be otherwise a unitary conductive path.

In an embodiment, conductive material (e.g. metal) plated polymeric fibres are used as the first and second conductive paths and/or as the leads, such as silver plated nylon thread. Alternatively, conductive wires could be used, such as stainless steel.

In an embodiment, the insulating layer is a back sheet of the absorbent article made of liquid impermeable material.

In an embodiment, the leads are oriented longitudinally and the conductive paths are oriented laterally. The laterally oriented conductive paths are longitudinally spaced from one another.

In certain embodiments, one of the first and second conductive paths is shared between two detection zones, thereby allowing a reduction in the number of conductive paths and thus the number of connections to a controller.

In a certain embodiment, the first and second conductive paths are positioned beneath a top surface of an absorbent core of the absorbent article. Thus, the conductive paths could be embedded in the absorbent core or positioned beneath the absorbent core. The conductive paths can be positioned beneath the absorbent core, yet still in electrical contact therewith. Embedding the paths in the core tends to reduce movement sensitivity of the sensor, while locating the paths between the core and a back sheet of the absorbent article provides improved liquid discharge sensitivity. In an embodiment, the absorbent core may be made of a lower layer of absorbent core material and an upper layer of absorbent core material that is smaller in size when the absorbent article is viewed in plan and laid out flat. Alternatively, the lower layer may have a different absorbent material composition, e.g. superabsorbent to fluff ratio, than the upper layer. In either case, the first and second conductive paths may be located between the lower and upper layers of the absorbent core.

The first and second conductive paths may be sewn into the absorbent article by passing through a back sheet of the absorbent article.

In a certain embodiment, the article is an adult incontinence diaper and paths are longitudinally spaced by a distance of 3 to 8 cm, 3 to 6 cm, or 4 to 5 cm, and are adjacent conductive paths, which gives an optimal trade-off between covering a full longitudinal extent of the absorbent core, reducing the number of leads and contacts required, and ensuring a sufficiently dense spread of detection zones to detect a first, or a low volume liquid discharge.

In an embodiment, there are at least 3 conductive paths providing at least 2 detection zones, wherein the conductive paths are evenly distributed along the absorbent core.

In an embodiment, each detection zone is formed by adjacent conductive paths.

In a certain embodiment, there is provided a system that includes the absorbent article described above and a control unit, wherein the control unit is configured to measure an electrical property between the first and second conductive paths to allow detection of when the liquid discharge is present between the first and second conductive paths and to do so for each of the plurality of detection zones.

The control unit is configured to apply an electrical potential between the first and second conductive paths and determine the electrical property from any returned current.

The controller is thus able to detect which, if any, zones the liquid discharge is in, which will be an indication of the spread of liquid discharge and thus also the volume of the liquid discharge.

In particular embodiments, the control unit is configured to measure the plurality of zones sequentially to avoid interference between each measurement and to simplify a switching structure in the control unit.

In particular embodiments, the control unit is configured to apply a pulse of electrical energy to each zone and to take the impedance measurement using the pulse. The pulse may be of the order of $1/10$ of a second or less. A pulse of electrical energy is one that is applied in discrete bursts of electrical energy separated by a rest time, as compared to continuous application of energy. Thus, the control unit may turn on the voltage application between the conductive paths for a limited amount of time and turn it off for a longer period of time between the on times.

In particular embodiments, it is not just the presence or not of a conductive path existing between the first and second conductive paths, but an indicator of the degree of electrical conductance that is measured (e.g. an impedance measurement). The degree of conductance is indicative of how close the absorbent article is to saturation in that zone, which allows a better estimation of the liquid discharge volume. Thus, the measured electrical property can be one that changes in scale or extent depending on how much liquid there is between the first and second conductive paths as a result of the impedance or resistance to electrical current flowing through the absorbent core between the first and second conductive paths decreasing with increasing wetness (the degree of change of the electrical property with liquid discharge quantity may reduce significantly towards core saturation).

In a second aspect, there is provided an absorbent article for absorbing liquid discharges of a wearer when worn in the crotch region of the wearer, the absorbent article including first and second electrically conductive paths that are electrically isolated from one another and which are disposed along a periphery of the absorbent article such that a liquid discharge of the wearer that spreads to being between the first and second conductive paths provides a conductive path therebetween, which enables leak detection to be carried out.

The above absorbent article enables leakage detection since any liquid discharge that reaches the periphery of the absorbent article is indicative of a leaking article.

In certain embodiments, the first and second conductive paths are positioned peripherally outside of an absorbent core of the absorbent article when the absorbent article is viewed in plan when laid out flat. This thus provides an indication that liquid discharge has spread beyond the absorbent core, which is indicative of a leaking article.

In certain embodiments, the absorbent article has first and second side edges shaped to fit with the legs of a wearer and the first and second conductive paths are arranged along at least one of the side edges. It is in the crotch or leg region of the absorbent article that leakage detection functionality is considered to be most effective.

In certain embodiments, the first and second conductive paths are positioned along a leg elastic portion of the absorbent article on at least one side of the absorbent article.

In a particular embodiment, there is provided a system including a control unit and the absorbent article described above, wherein the control unit is configured to apply a potential between the first and second conductive paths and measure an electrical property between them to allow determination of whether liquid discharge has spread to a position between the first and second conductive paths.

In a particular embodiment, the system includes an analysis module configured to compare the measured electrical property to a predetermined threshold and to make a determination that a leakage state of the absorbent article has been reached if the predetermined threshold has been exceeded, wherein the predetermined threshold is set to distinguish over conductance between the first and second conductive paths as a result of electrical conduction through the skin of the wearer or through moisture from the skin of the wearer as compared to saturation as a result of liquid discharge leakage.

In yet another aspect, there is provided an absorbent article analysis system comprising an absorbent article for absorbing liquid discharge of a wearer when worn in the crotch region of the wearer and a position sensor that is able to output a position signal enabling differentiation between a lying position and a sitting position of the wearer, a liquid discharge detector that is able to output a liquid discharge signal indicative of a wetness state of the absorbent article, wherein an analysis module is configured to record the position output signal and the liquid discharge signal to thereby correlate the position signal and the liquid discharge signal over time.

The analysis system thus allows one to analyse any time patterns when liquid discharge occurs and also any patterns in terms of liquid discharge as a result of movement or position change. The analysis system is particularly useful in diagnosing stress incontinence since it can be determined that a change in position from lying to standing has occurred at roughly the same time as a liquid discharge event, which could be taken as indicative of a wearer having stress incontinence.

The position sensor can be provided as part of a control unit attached to the absorbent article. In certain embodiments, the position sensor is arranged at a front waist region of the absorbent article, so as to be generally centrally located with respect to the wearer's torso. It has been found that arranging the position sensor on the front of the absorbent article allows a strong wearer related movement signal to be obtained. In certain embodiments, the position sensor is an accelerometer. An accelerometer or other appropriate position sensor is configured to issue a signal that is able to differentiate lying, sitting, standing, and moving states of the wearer, which is useful information in determining urination patterns for a wearer and as a diagnostics tool. The position sensor can be further configured to issue the position output signal such that a plurality of lying orientations are differentiable including at least one of lying on back, lying on front, lying on side, lying on left side and lying on right side.

The analysis tool can be configured to output a parameter indicating a mobility of a wearer based on amount of time the wearer is determined to be in a standing state, perhaps as compared to a sitting or lying state.

In a further embodiment, the liquid detector includes a plurality of liquid discharge detection sensors so that the analysis module records the wetness state in a plurality of detection zones distributed about the absorbent article. The system thus allows liquid discharge detection at a number of positions on the absorbent article to be measured, perhaps also in conjunction with determination of one of a number of different positions of the wearer to be correlated against time of the various events, which provides highly useful absorbent article performance data as well as useful diagnostic information concerning the wearer.

The use of a number of detection zones allows the spread of the liquid discharge over time to be tracked. In certain embodiments, an output module is configured to output a display of the spread of liquid discharge over time. The detection zones can be longitudinally distributed with respect to one another, along at least 50%, 60%, 70%, 80%, or 90% of a full longitudinal extent of the absorbent core of the absorbent article when viewed in plan with the absorbent article laid out flat.

Further, the system enables differentiation of a first and at least one subsequent liquid discharge event based on a change in the number of zones that are determined to be wetted or based on a change of electrical property in a given zone indicating increased wetness as detected by the corresponding liquid discharge sensor.

In certain embodiments, the liquid detector includes a measurement module that is configured to measure an electrical property (e.g. impedance) of a detection sensor indicative of the degree of wetness in a given liquid discharge detection zone so that the analysis module is able to record the degree of wetness for a given liquid discharge detection zone or a plurality of liquid discharge detection zones. In this way, not only can the presence or otherwise of liquid be determined, but also how wet the zone is, which offers useful analysis information.

In a particular embodiment, an output module is configured to output display information showing the measured electrical property over time (which indicates liquid discharge events and perhaps also the degree of liquid discharge), respectively for each given zone and also including position data differentiating for example lying and standing positions and at what time. In a yet more particular embodiment, leakage data shows the occurrence of a leakage event and at what time. In certain embodiments, the output module is configured to output a parameter indicative of a liquid discharge volume calculation performed by the analysis module. The output module may display the information on a light emitting screen, as a print-out or in other known ways.

In a particular embodiment, the data from the output signals is stored in a hard memory with the associated time. The use of a hard memory device means that the system is not required to be provided with data transmitters for each absorbent article and a receiver at each location in which the system is set up. Instead, the absorbent article can be provided with a control unit mounted thereon and having as part of the control unit the hard memory, thereby providing a system with reduced set-up complexity. The analysis software can retrieve the data from the hard memory and perform analytical operations thereon.

In certain embodiments, the correlation over time is done with respect to a 24 hour clock in local time so that one can work out when the liquid discharge occurs and the positions of the wearer with respect to local time. This may be useful since, for example, whether the liquid discharge happens at night or day is interesting.

In a particular embodiment, the analysis module is configured to determine a saturation condition of the liquid detection zone from the measured electrical property and calculate a volume of liquid discharge from the number of saturated liquid detection zones. It has been found that this method of detecting liquid discharge volume is particularly accurate as compared to other methods tried.

In certain embodiments, the system further includes a leakage detector that is configured to output a leakage signal indicative of leakage from the sides or ends of the absorbent article and the analysis module is configured to correlate the position signal, the liquid discharge detection signal and the leakage signal over time. In this way, the system is able to provide useful information on the causes of absorbent article leakage, which may well prove helpful in evaluating absorbent article performance.

In an embodiment, each of the signals, e.g. liquid discharge, position, etc. are generated and recorded at regular intervals.

In another aspect, there is provided a system including a control unit and an absorbent article, the absorbent article for absorbing liquid discharge of a wearer when the absorbent article is worn in the crotch region of the wearer, the absorbent article including a liquid discharge sensor that detects liquid discharge on the basis of a change in electrical property when the absorbent article is wetted, wherein the control unit is configured to subject the liquid discharge sensor to pulses of electrical energy in order to take measurements of the electrical property with each pulse, wherein the pulses are separated by an electrical energy rest period.

The electrical property may be measured by way of an oscilloscope, multimeter, voltage divider or other known means.

The pulsed operation of the system has at least two advantages. A first advantage is that it saves battery power as compared to a constant voltage being applied to the sensor. The rest period between the pulses is effectively a battery sleep mode. A second advantage is that it has been found that measuring the electrical property under extended current application can cause irregular measurements in a wet absorbent article.

In certain embodiments, the control unit includes a battery from which the pulsed electrical current is drawn. In certain embodiments, the control unit is mounted to the absorbent article.

Battery life is particularly important in the present system since it is required to work throughout a test period if the testing of the absorbent articles is to be implemented conveniently.

In another embodiment, the absorbent article includes a plurality of such liquid discharge sensors and the control unit is configured to apply a pulse of electrical energy to each of them, for example sequentially, in order to determine the electrical property for each liquid discharge sensor.

The sequential processing of each sensor avoids interference. In an embodiment, there are at least 3, 4, 5, 6 or more of such sensors, and the control unit is configured to apply the pulses of energy to each of them in a sequence that avoids adjacent pulses in time being applied to adjacent sensors in space. In an embodiment, each sensor is provided by first and second adjacent conductive paths that are electrically isolated when the absorbent core is dry and that have a conductive bridge between them extending through the absorbent core when the absorbent core is wet. In a particular embodiment, adjacent sensors share the middle conductive path as one of the first and second conductive paths. In an embodiment, the control unit is configured to apply a first pulse between first and second adjacent conductive paths of a first sensor and to apply a subsequent pulse between first and second adjacent conductive paths of a second non-adjacent sensor. Alternatively put, the second sensor and the first sensor are located with at least one intermediate sensor between them. This sequencing algorithm avoids interference between results of subsequent pulsings, which is also helped by the natural time interval between pulses.

In certain embodiments, the energy pulses are alternating current or direct current pulses. The pulses can be of a square wave form of short duration energy bursts separated by longer duration rest periods or more peaked forms of energy pulse.

The control unit may include a hard memory device onto which the measured electrical property is stored, for example in association with time. In a particular embodiment, the control unit includes a memory buffer and the control unit is configured to store a plurality of sequential electrical property measurements for a given liquid discharge sensor. The storage of data in the memory buffer and in the hard memory is powered by the battery. This enables battery saving since the storage in a memory buffer takes significantly less power than storage on the hard memory.

In particular embodiments, the pulses of electrical energy are not generated until the control unit has been contacted with a contact of the liquid discharge sensor. Thus, until the control unit is mounted to the absorbent article and appropriately electrically contacted therewith, the control unit is kept in a low power mode.

One implementation of this feature would be to have a contact on the absorbent article that acts as an on switch for the control unit when the contacts of the control unit are brought into electrical engagement with the contacts of the absorbent article.

In a yet further aspect, there is provided an absorbent article for absorbing liquid discharge of a wearer when the absorbent article is worn in the crotch region of a wearer, the absorbent article including a front sheet for transferring the liquid discharge into the absorbent article, a back sheet for preventing escape of the liquid discharge from the absorbent article and an absorbent core for absorbing the liquid discharge and which is captured between the front sheet and the back sheet. The absorbent article includes at least one liquid discharge detection sensor to detect a wetness condition of the absorbent article on the basis of an electrical property associated with the detection sensor and the absorbent core. The absorbent core has a Hardy integrity of at least 5 thrusts, of at least 10 thrusts, at least 20 thrusts, at least 30 thrusts, at least 50 thrusts, at least 60 thrusts, at least 70 thrusts, at least 80 thrusts or at least 90 thrusts. The Hardy integrity test procedure to be used in assessing the scope of this statement is described below.

It has been found that reliable liquid discharge detection results are reliant on high absorbent core integrity. It is speculated that during use, a low integrity absorbent core will partially break up when wet causing conductivity breaks in the core, preventing or reducing the accuracy of measurement of the electrical property.

In certain embodiments, the liquid discharge detection sensor includes first and second electrically isolated conductive paths and is operable by passing electrical current between the first and second conductive paths through the absorbent core when the absorbent core is wet and to measure the electrical property from the electrical current so passed.

DETAILED DESCRIPTION OF PREFERRED EMBODIMENTS

Absorbent Article and Liquid Discharge Sensor Arrangement

Figure 1:
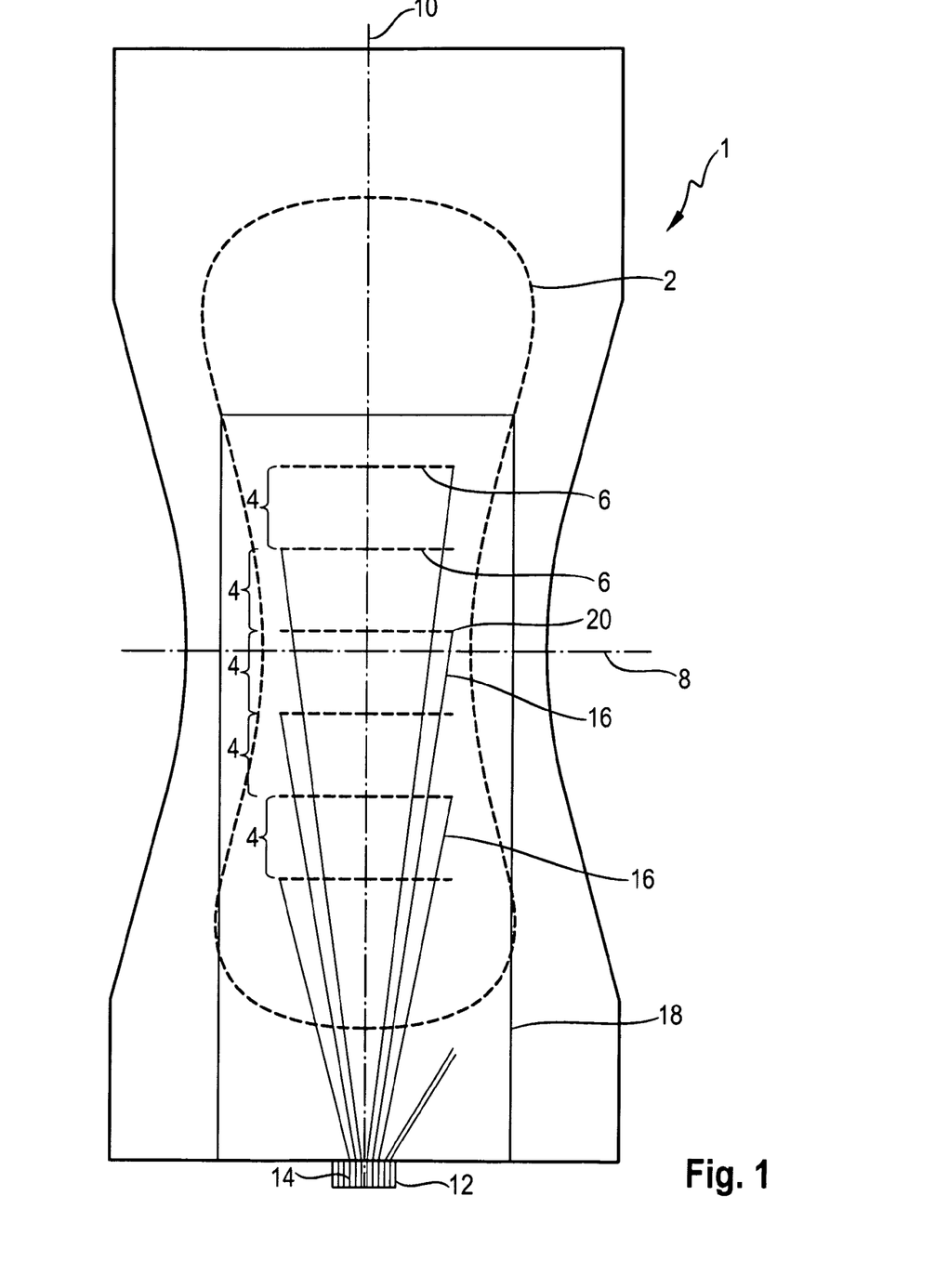
FIG. 1 shows a plan view of an absorbent article laid out flat and illustrates an arrangement of liquid discharge detecting threads in longitudinally spaced lateral lines.

FIG. 1 shows an absorbent article 1 that will generally include a top sheet, a back sheet and an absorbent core 2 captured therebetween. The absorbent article 1 is shown in the form of an adult incontinence diaper in FIG. 1. The principles of the present disclosure are, however, applicable to other absorbent articles such as baby or toddler diapers, sanitary towels or other known absorbent articles. The absorbent article 1 is an example of a conventional adult incontinence diaper except for the presence of a plurality of liquid discharge detection zones 4 (in this specific example, there are five liquid discharge detection zones 4).

The zones 4 are longitudinally distributed over about 50% of the full longitudinal extent of the absorbent core 2. The longitudinal position of the zones 4 is shifted more toward a front region of the absorbent article than a rear region so as to be more likely to directly receive any urination. The zones 4 extend laterally for about 60% of the full lateral width of the absorbent core 2 for the front most and rear most zones 4 and about 80% for the zone 4 located closest to the absorbent core's laterally thinnest point.

Each zone 4 includes first and second electrically conductive paths 6 (in the form of electrically conductive threads) that are each aligned with the lateral axis 8 of the absorbent article 1 and are longitudinally spaced from one another along the longitudinal axis 10 of the absorbent article 1. The conductive paths 6 are in physical and electrical contact with the absorbent core 2. The end zones 4 share a conductive thread 6 with an adjacent zone, while the middle zones 4 share both conductive threads 6 with their adjacent zones 4.

The absorbent article 1 includes a control unit contact area 12 to which a control unit is to be connected in order to activate each of the zones 4 to get a liquid discharge reading. The contact area 12 is located at a laterally central front waist region of the absorbent article 1. The contact area 12 includes a plurality of electrical contacts 14 for making electrical contact with corresponding contacts on the control unit. Each conductive path 6 is connected to a respective electrical contact 14 by way of a respective electrically conductive lead 16. The combination of a given contact 14, a lead 16 and a conductive path 6 is formed of a unitary structure (a conductive thread) in this embodiment, as will be made clearer in the following. The leads 16 extend along the shortest path from the conductive path 6 to the corresponding contact 14. Although not shown, the contact area 12 includes a blind contact that the control unit is configured to sense to determine an "on" or "mounted to absorbent article" condition.

The conductive path 6 can be distinguished from the lead 16 because the conductive path 6 is in direct physical and electrical contact with the absorbent core 2, while the lead 16 is not, so that it can be electrically isolated from the absorbent core 2. More specifically, the conductive paths 6 are on the absorbent core side of the back sheet and in electrical and physical contact with the absorbent core 2. The leads 16 are located on the other side of the back sheet so that the back sheet offers electrical insulation between the absorbent core 2 and the leads 16. A liquid impermeable or hydrophobic cover sheet is laid over the leads 16 on the outside of the back sheet so as to avoid erroneous liquid discharge detection readings as a result of the outside of the absorbent article 1 coming into contact with moisture (e.g. because of the wearer sitting on a damp surface). The leads 16 each pass through the back sheet at the points 20. One end of each conductive path 6 terminates without a return path to the contact area 12. Accordingly, a return path can only be established by current passing from one contact 14 through one lead 16 and one conductive path 6 and returning through an adjacent conductive path 6 and its lead 16 by current passing across a space between the adjacent conductive paths 6 as a result of the absorbent core 2 becoming wetted in the space.

In a particular embodiment, each contact 14, lead 16 and conductive path 6 is made of a unitary thread that has been coated with electrically conductive material (e.g. metal or carbon or conductive polymers).

The absorbent article 1 can be made by taking a conventional absorbent article such as a Tena Flex Medium ("Super" absorbency level), which is commercially available, and modifying it so as to include the coated threads. More specifically, a needle with a thread attached is pierced through the back sheet of the absorbent article 1 so that a part of the thread is located on one side of the back sheet to provide the conductive path 6 in electrical communication with the absorbent core 2 and another part is located on the other side of the back sheet to provide the lead 16. The conductive path 6 part is glued according to the laterally aligned extension with one end of the thread terminating at one end of the conductive path as shown in FIG. 1. The lead 16 part of the thread is glued in place following the extension shown in FIG. 1 so as to extend to the front waist edge and marginally beyond it. This is repeated for each conductive thread. A cover sheet 18 is laminated over the leads 16 and the outside of the back sheet to keep the leads in position and to provide a liquid barrier. A tab of tape protruding beyond the front waist edge is used to secure the contact terminal ends of the conductive threads at the contact area 12.

Leakage Detection

Figures 2A, 2B:
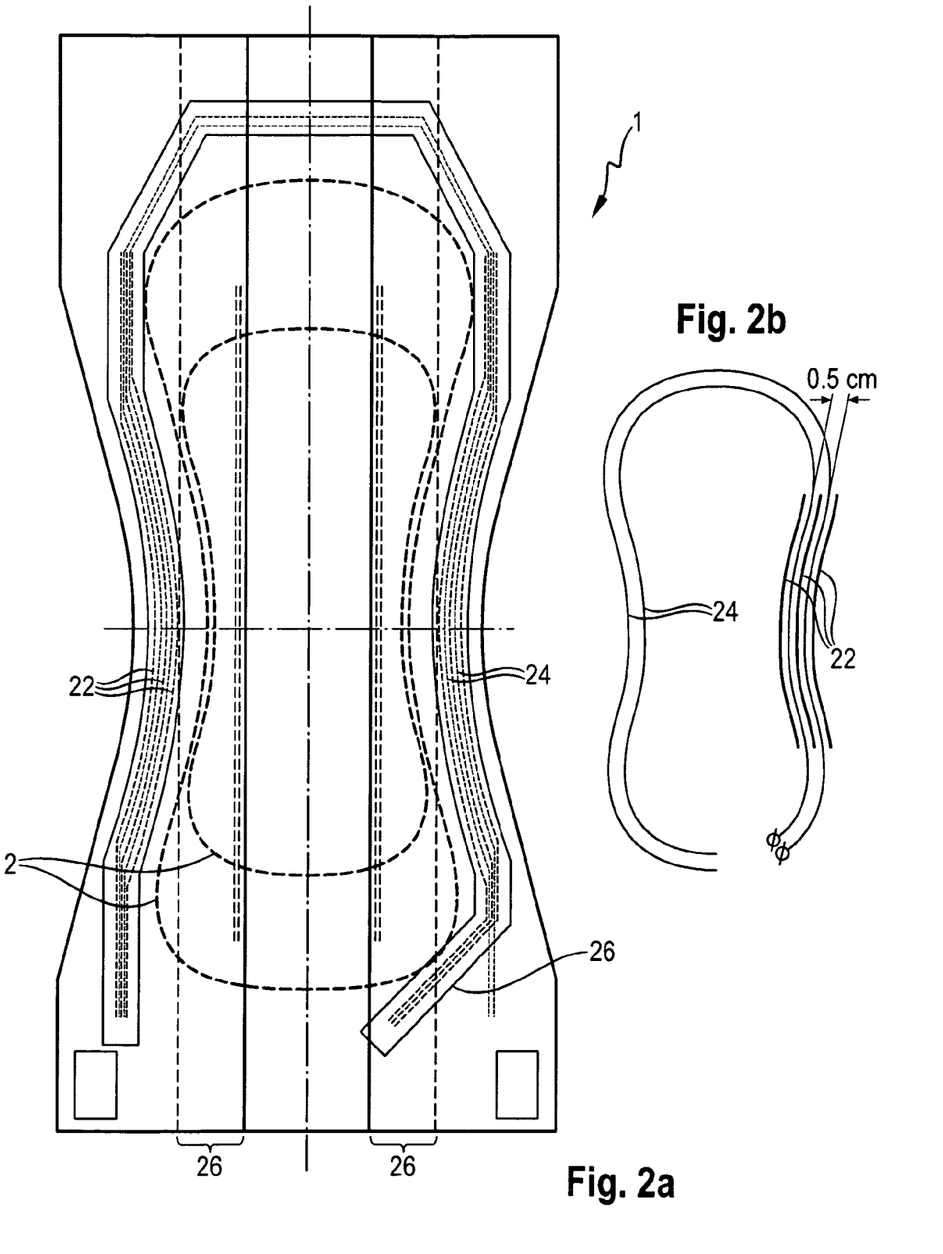
FIG. 2a discloses an absorbent article with a leakage detection mechanism emphasised rather than a liquid discharge detection mechanism as in FIG. 1.
FIG. 2b is a conceptual diagram illustrating the placement of threads of the leakage detector in greater detail with respect to leg elastics.

In FIG. 2a, an absorbent article 1 is shown in a flat laid out configuration. The absorbent article 1 has first and second leakage detection conductive paths 24 extending around a periphery of the absorbent article 1. The conductive paths 24 follow each other's path but are marginally spaced apart so that an electrically conductive path is only established between them when a liquid discharge is in the space between them. In the specific configuration shown, the conductive paths 24 extend around three sides of the absorbent core 2 to provide a border about the absorbent core 2. The conductive paths 24 are disposed peripherally outside of the absorbent core 2 and also outside of standing gathers 26 of the absorbent article 1. The conductive paths 24 follow the leg elastics 22 and are disposed laterally at about the same location as the leg elastics 22. In FIG. 2b, it can be seen that the conductive paths 24 are arranged intermittent three leg elastics 22.

The conductive paths 24 terminate at one end at the contact area 12 (not shown in FIG. 2—see FIG. 1), then extend along the left leg elastics 24, around the rear waist side of the absorbent core 2, extend along the right leg elastics 24 and finally terminate in the front waist region of the absorbent article 1. The contact termination of the conductive paths 24 in the contact area 12 offers a pair of contacts for contacting with corresponding contacts in the control unit.

The conductive paths 24 are positioned between the layers that the leg elastics 22 are sandwiched between. This is done by threading a conductive thread attached to a needle in order to pierce the layers. In order to avoid erroneous leakage detection impedance readings as a result of external moisture, a liquid impermeable cover layer is placed and adhered over the outer layer to cover the conductive paths 24.

Control Unit

The control unit of a particular embodiment will now be described without reference to a figure disclosing the structural form of the control unit. The control unit includes contacts to engage with the contacts 14 of the protruding tab of tape of the absorbent article 1. The control unit has a main casing with teeth protruding from the casing to engage with the contact wires 14 of the absorbent article 1. The teeth thus provide the contacts of the control unit.

The control unit includes a memory card to provide hard memory, a memory buffer, an impedance measurement circuit, an accelerometer, a clock, a processor, and a battery. The battery is used to power operation of all of the components of the control unit. The elements of the control unit just listed can be stored within an openable and closeable casing. The casing can have a fastener thereon, such as a hook fastener (i.e. the hook component of Velcro RTM ), for securing it to an outer casing of the absorbent article 1. The control unit is designed to be mounted centrally at a front waist region of the absorbent article 1. The control unit is configured to only keep powered circuits that can not be switched off before the control unit is contacted with the contacts 14 of the absorbent article. More specifically, the control unit is in a mode whereby only essential circuits are kept powered until the blind contact of the absorbent article is sensed. Thus, the clock must be kept powered even before the control unit is mounted to the absorbent article 1, but the impedance measurement or accelerometer (discussed below) circuit does not need to be supplied with power at this time. The joining of the contacts of the control unit to the contacts 14 of the absorbent article 1 acts a switch to go into an active operation state so that, for example, the impedance measurement circuit is powered. This is a battery saving feature.

The accelerometer is configured to output a different signal depending on whether the wearer of the control unit and absorbent article 1 combination is lying, sitting or standing. The accelerometer may also issue a different signal depending on whether the wearer is lying on his/her front, back, left side or right side, or is active for a period of time such as walking.

The impedance measurement circuit is configured to regularly apply a potential between adjacent pairs of conductive paths 6 of the absorbent article 1 and measure or indicator of the impedance therebetween. Generally speaking, the lower the impedance measurement then the wetter the absorbent core 2. The responsiveness of the absorbent core 2 to wetness as the absorbent core 2 reaches saturation between the adjacent conductive paths 6 is significantly lower than when the absorbent core 2 is only slightly wetted. The impedance measurement circuit applies the potential between adjacent conductive path 6 pairs sequentially. To do so, the impedance measurement circuit switches between pairs of contacts 14 until an impedance measurement or other electrical property between the conductive paths 6 that changes in dependence on core wetness has been performed for the full complement of adjacent pairs of conductive paths 6. In order to save the battery resource, there is a rest time between the potential being applied to each pair that is greater than the duration of the electric potential application, thereby activating the adjacent conductive paths 6 with "pulses" of electrical energy in doing the impedance or other electrical property measurement. In fact, the sum of the duration of the current pulses for each adjacent pair of conductive paths 6 is shorter in duration than the rest time between pulses for any given adjacent pair of conductive paths 6. Example durations are a rest time of one second between sequential current pulses for a given pair of adjacent conductive paths 6 and less than 0.1 second to multiplex through the full complement of pairs of adjacent conductive paths 6.

The processor is configured to take the impedance measurements from the impedance measurement circuit and store them in the buffer until a sequence of a set of measurements for all of the pairs is stored in the buffer. The processor is further configured to take an accelerometer reading for each set of impedance measurements and store that in the buffer memory. The processor is further configured to store a clock reading with each set of accelerometer and impedance measurements. The storage of this set of data is repeated regularly (e.g. every second as described above) until the buffer memory is full or near full. At this time, the processor is configured to transfer the data from the buffer memory to write it into the memory card. The buffer memory allows the number of memory card writing operations to be reduced, which is a significant power saver for the battery since writing the memory card is relatively power intensive.

The memory card is removable so that the stored data can be accessed by remotely located analysis software. The stored data can alternatively be accessed by a cable, a USC connection or the like. In such instances, other implementations of the hard memory than a memory card may be used.

Analysis Module

An analysis module, which is implemented by way of software, is used to process the stored data into a useful form for an analysis of the performance of the absorbent article and for other purposes such as for diagnostic reasons. A card reader is used to retrieve the data and input it into the analysis module. In a particular embodiment, the analysis module takes the data and outputs it to a display in a conveniently readable form. An example output is for the analysis module to present a graph of impedance with a different colour line for each of the various zones so that the degree of wetting in each of the zones and its progress over time can be viewed by a user of the analysis software.

The analysis module takes the impedance data for each of the zones from the memory card and runs it through a filter to smoothen the data out so as to present clear peaks for when a liquid discharge event has taken place and to soften any noise attributes in the data. Impedance peaks in the graph will show the time at which a liquid discharge event has occurred and in which zones and will also show how the liquid discharge spreads through the absorbent article over time. The graph will allow a user of the analysis software to determine when initial urination took place and also whether any subsequent liquid discharges occurred. To be able to view the spread of the liquid discharge over time is useful information for assessing the absorbency performance of the absorbent article. To be able to see when and how often liquid discharge took place is useful in diagnosing a particular type of incontinence such as drip incontinence and is also useful in identifying liquid discharge patterns, which will enable a care giver to optimise the time when an absorbent article is changed for a dry replacement absorbent article in order to minimise the amount of time the wearer is subjected to a wet absorbent article.

One exemplary way of determining individual liquid discharge events is to analyse the measured data of the electrical property measured between the conductive paths that change in dependence or how wet the absorbent core is in a conduction path through the absorbent core. It has been found that the electrical property, particularly impedance, raises to a peak (or troughs) when the liquid discharge is first received between the first and second conductive paths and then settles. The pattern when plotted is distinct and relatively easily spotted. This may be as a result of the increased temperatures of a fresh liquid discharge to a settled one or because of its initial flow as compared to a stagnant liquid discharge. Accordingly, the analysis module may be configured to monitor the measured electrical property over time to determine these peaks (or troughs) to make a determination of individual liquid discharge events. Alternatively, the measured electrical property over time data could be outputted to a user in such a way (e.g. graph of sufficient time resolution) for the user to make out each individual liquid discharge.

As well as a graph form for the data, the analysis module also allows viewing the spread of liquid discharge over time by a graphic of the absorbent article and the various zones, where the wet zones are illustrated in a different colour or shading to the dry zones and which can be scrolled through in time to show the progress of the liquid discharge and subsequent liquid discharges in a user intuitive manner.

The analysis module is also configured to display the accelerometer and leakage detection readings on the graph of impedance versus time so that a user can determine the position of the wearer of the absorbent article during liquid discharge and also throughout the time when the absorbent article is worn to determine the liquid discharge conditions and the standing position of the wearer when leakage has occurred. The accelerometer provides useful diagnostic information in conjunction with the liquid discharge information because if a liquid discharge is consistently coincident with a wearer transitioning from a lying to a sitting state or from a sitting to a standing state, this is indicative of the wearer suffering from stress incontinence. Being able to determine the position that a wearer is in and also the liquid discharge situation when leakage occurs will be useful information for analysing the cause of a liquid discharge leakage.

In order to avoid erroneous determinations of liquid discharge leakage because of current passing between the first and second conductive paths through the skin, particularly through moist skin, the analysis module compares the impedance measured in the leakage circuit to a predetermined threshold and does not indicate in the graph that a leakage has occurred until the impedance dips below the threshold, which thereby ensures that a leakage is only represented when a leakage has actually occurred.

If a system of diapers was set up in a nursing home, the analysis module is able to output information relevant to the quality of care being given to the wearers. One example of an interesting statistic that the analysis module could be configured to output is the average amount of time that a wearer suffers from wearing a wet absorbent article. If the average amount of time exceeds acceptable limits, the user of the software is made aware of the poverty of care being given.

The analysis module may further be configured to output an estimated volume of urination, which is useful for product developers in assessing the effectiveness of the absorbent article and is useful information for a care giver in determining whether the right absorbency level absorbent article is being worn. The analysis module is configured to determine from the impedance level whether a particular zone has reached saturation point. The impedance level at which saturation occurs is a predetermined parameter of the analysis module as is the amount of liquid at saturation. From the number of zones that have reached saturation point, the analysis module is able to calculate an acceptably good estimate of liquid discharge volume. A more sophisticated estimation of liquid discharge volume could be performed by correlating impedance to amount of liquid absorbed in a particular liquid detection zone before saturation occurs, which may allow relatively small liquid discharge volumes to be calculated such as happens for a wearer suffering from drip incontinence.

It is also useful to determine the length of time, particularly in a system of absorbent articles, before a first liquid discharge event. The data stored in the memory card begins at time zero when the control unit is first contacted with the contacts of the absorbent article. The output module is thus configured to determine the length of time from when data is first recorded for that absorbent article to when the impedance measurement shows that a first liquid discharge event has occurred. The analysis module is configured to output this information.

Use

To use the system described above, a user takes an absorbent article 1 having the liquid discharge detection zones 4 as shown in FIG. 1 and the leakage detection conductive paths 24 as shown in FIG. 2. A control unit, which, in particular embodiments, is minimised in size, is attached to a front waist region of the absorbent article 1 by way of the hook portion of conventional hook and loop fastening means and so that a respective one of the teeth of the control unit is engaged with a corresponding contact 14 in the contact area 12 of the absorbent article 1. The absorbent article is mounted to a wearer so that the control unit is able to monitor and record in the hard memory data concerning liquid discharge events and the position at any given time of the wearer.

As the control unit and the absorbent article are contacted as described above, the impedance measurement circuit begins to collect data, as does the accelerometer. Thus, the impedance measurement circuit of the control unit will apply for a short duration (less than one tenth of a second) an electric potential between the first and second conductive paths 6 of one of the liquid discharge detection zones 4 and will repeat the operation for each of the liquid discharge detection zones 4 in turn. The impedance between the first and second conductive paths 6 in each of the detection zones 4 is taken and stored in the buffer memory. The impedance measurement circuit then applies a potential between the first and second conductive paths 24 of the leakage detection means (again for a duration of less than $\frac{1}{10}$ of a second) and records the obtained impedance data into the buffer memory of the control unit. A position measurement from the accelerometer is also taken by the processor of the control unit and stored in the buffer memory. A rest time of the order of 1 second is then allowed to elapse before the same measurements are taken so as to record in the buffer memory a subsequent set of data. This process is repeated until the buffer memory is full and at which time a single memory card writing step is performed to transfer the data from the buffer memory to the memory card. This process of collecting data is repeated for the lifetime of use of the control unit and the absorbent article.

If the user is lying down, the accelerometer is able to distinguish this state in its output signal and also to distinguish whether the wearer is lying on his/her front, back or side (and perhaps also whether the left side or the right side).

If the wearer urinates, current is able to flow between the first and second conductive paths 6 of the liquid discharge detection zone 4 in which the urination initially takes place. This will cause a change in impedance that the control unit is able to detect and record. Second by second as the urination spreads through the liquid discharge detection zones 4, the impedance change in the other zones 4 can be detected and recorded. Accordingly, the spread of the urination can be determined by the analysis software as can the speed of its progress and the extent of its progress. If certain of the detection zones 4 become saturated, and there is a second urination event, the zones 4 that have not yet been saturated or activated will provide a change of impedance in the output signal for those zones 4, which will thus allow the analysis software to pick up on a subsequent liquid discharge event.

If liquid discharge is able to spread beyond the absorbent core 2 and pass to the peripheral conductive paths 24 so as to reach the leg elastic 22 area, then when a potential is applied between the first and second conductive paths 24, the impedance measurement circuit will record a change of impedance. The analysis software will be able to compare the recorded impedance between the conductive paths 24 to a predetermined threshold and determine that a leakage has occurred.

When it comes time to replace the absorbent article 1 with a fresh absorbent article, the control unit can be mounted to the new absorbent article in the manner described above. The analysis module is able to determine that a data break occurred as a result of the control unit going into a passive state once the contacts 14 of the absorbent article 1 of the first absorbent article 1 were disengaged. The control unit has an identifier that is uniquely identifiable by the analysis module so as to allow it to be differentiated from other control units. If the analysis is to perform a patient diagnostic function, then a particular control unit should be kept for use with the same patient so that all of the data recorded by that control unit can be associated with the patient.

When it is time to retrieve the data, the control unit is dismounted from the absorbent article 1 and the memory card is removed. The memory card is placed in a memory card reader of the analysis module so that the analysis module can retrieve the data to perform data analysis operations as described above.

Alternatives

In the above embodiments, the conductive paths 6, 24 of the liquid discharge detection zones 4 and the leakage detector are implemented by way of a thread that has been coated with an electrically conductive material. The conductive paths 6, 24 could instead be implemented by electrically conductive ink printed onto the absorbent article 1 or on a carrier integrated into the article. The carrier could instead of being printed with conductive ink, it could be provided with conductive threads, which may offer benefits in terms of manufacturing efficiency, particularly when manufacturing on mass.

The conductive paths 6 of the liquid discharge detection zones 4 shown in FIG. 1 are straight and perfectly laterally aligned. It is important for the conductive paths 6 to extend from adjacent one side of the absorbent core to adjacent the other side of the absorbent core 2 so that a liquid discharge event is detected even if the liquid discharge is off centre or restricted to a small lateral portion of the absorbent core 2. It is envisioned that the conductive paths 6 may be wavy or straight as shown.

Alternatively, the conductive paths 6 may extend at an angle to the lateral axis 8 so as to individually define a shallow v-shape and to define in combination with an adjacent path a diamond shape. Many other configurations for the laterally extending conductive paths 6 are envisaged.

The conductive paths 6 shown in FIG. 1 are regularly spaced in the longitudinal direction. It is possible, however, to implement the conductive paths so that they are more densely spaced in the longitudinal direction at an area of the absorbent core 2 that is likely to receive the most urination.

Referring to FIG. 2a, it is possible to separate the conductive paths 24 into a left side leakage detection zone including first and second conductive paths and a right side leakage detection zone including first and second conductive paths and having a corresponding pair of contacts in the contact area 12 for both the left side leakage detection zone and the right side leakage detection zone. In this way, the leakage detection data identifies which side of the absorbent article 1 that the leakage occurred.

In FIG. 1, there are shown five liquid discharge detection zones 4. Other numbers could, of course, be used. An absorbent article having 10 such liquid detection zones, for example, is envisioned.

The conductive paths 24 of FIG. 2 are positioned in between leg elastics 24. Another possible implementation would be to have the conductive paths 24 positioned outside of the leg elastics which may offer detection that liquid discharge has not only exited the absorbent core 2, but also gone beyond the leg elastics and thus external of the external article 1 (and likely has run onto the wearer's legs).

The control unit described above has a memory card for recording the data. It is possible, however, that the control unit could be provided with a wireless transmitter so that data recording could be done remotely such as on a hard memory in a central computer at, for example, a nursing home. This could save battery power when the wireless transmitter uses less power than it takes to record the data on a hard memory as provided as part of the control unit. In another variation, the wireless transmitter and the memory card could be provided as part of the control unit to provide data recording redundancy to avoid loss of information.

In the above description of the impedance measurement circuit, the impedance measurement circuit is configured to begin taking measurements at regular intervals once the control unit is electrically contacted with the contacts 14 of the absorbent article 1. One possibility would be to record the data at extended intervals until a first liquid discharge event is indicated by the impedance measurement circuit and thereafter record data more frequently. This allows memory and battery to be saved, while also ensuring sufficient data density when it is required.

Hardy-Core Integrity Test

Purpose and Field of Application of the Hardy Test

This method is designed to measure how many times an absorbent product can be raised and dropped 40 mm before the core of the product breaks down.

Principle

The absorbent product is subject to repeated physical stress by raising and dropping it until the core breaks apart. The number of drops before the core breaks is used to evaluate the strength of the core.

Preparation

The absorbent product is stored for 24±4 h at 50±10% r.h. and 23±1° C. before testing.

Cut up all the elastic, without doing damage to the core, so that the product can hang straight down.

Dispense 0.9 sodium chloride solution to the product so that an even distribution occurs. Liquid amount is set to approximately 1/7 of the absorbent products Rothwell value (ISO 11948-1)

Let the product rest for 12 minutes.

Secure the product in clamps so that it hangs in a flat perpendicular position resting against a plain surface.

Drop the product 40 mm. Repeat 100 times or until the core breaks with a drop rate of 10 drops/minute.

Note the number of drops before core breaks.

The invention claimed is:

1. An absorbent article for absorbing liquid discharge when worn on the crotch region of the body of a user, the absorbent article comprising a plurality of detection zones for detecting the liquid discharge, each detection zone provided by first and second electrically conductive paths that are electrically isolated from one another and arranged so that a liquid discharge between the first and second conductive paths allows electrical current to flow between the first and second conductive paths which is able to be detected to detect the presence of liquid discharge in the respective zone, wherein the plurality of zones are longitudinally distributed with respect to the absorbent article along an absorbent core of the absorbent article, to allow the longitudinal extent of the discharge to be ascertained, wherein the first and second conductive paths are each connected to contacts for electrically contacting the first and second conductive paths to a control unit by respective first and second leads that are insulated from the absorbent core of the absorbent article, wherein the first and second electrical paths are laterally aligned and in electrical contact with the absorbent core.

2. The absorbent article of claim 1, comprising a top sheet for allowing the liquid discharge to enter to the absorbent article and a back sheet for preventing the liquid discharge from escaping the absorbent article and the absorbent core captured between them, wherein the zones are distributed along at least 30% of the longitudinal extent of the absorbent core.

3. The absorbent article of claim 1, wherein there are at least three detection zones.

4. The absorbent article of claim 1, comprising a back sheet for preventing the liquid discharge from escaping from the back of the absorbent article and a top sheet for allowing the liquid discharge to enter the absorbent article and which together capture an absorbent core, the first and second conductive paths extending laterally at least about 50% of the lateral extent of the absorbent core at their respective location.

5. The absorbent article of claim 1, wherein the first and second conductive paths are longitudinally spaced from one another.

6. The absorbent article of claim 1, wherein the first and second conductive paths are elongate.

7. The absorbent article of claim 1, wherein at least one of the first and second conductive paths is shared between adjacent detection zones.

8. The absorbent article of claim 1, wherein the contacts for each of the leads are arranged in a control unit contact area of the absorbent article.

9. The absorbent article of claim 1, wherein the respective leads are arranged on one side of an electrically insulative layer of the absorbent article and the first and second conductive paths are arranged on the other side of the insulative layer to be in electrical contact with the absorbent core.

10. The absorbent article of claim 1, wherein the first and second conductive paths are positioned beneath a top surface of an absorbent core of the absorbent article, yet still in electrical contact therewith.

11. The absorbent article of claim 1, wherein the conductive paths are positioned beneath the absorbent core, yet still in electrical contact therewith.

12. A system comprising the absorbent article of claim 1 and a control unit, wherein the control unit is configured to measure an electrical property between the first and second conductive paths to allow detection of when the liquid discharge is present between the first and second conductive paths and to do so for each of the plurality of detection zones.

13. The system of claim 12, wherein the control unit is configured to measure the plurality of zones sequentially.

14. The system of claim 12, wherein an indicator of the degree of conductance between the first and second paths through material of the absorbent article is measured as the electrical property, which changes in dependence on the wetness of the absorbent article material between the first and second conductive paths.

15. The system of claim 12, wherein the control unit is configured to apply a potential between the first and second conductive paths in the form of an electrical energy pulse.

16. The system of claim 15, wherein the electrical energy pulse is of a duration less than 0.1 seconds and is separated from a preceding pulse by a rest time.

17. The system of claim 16, wherein the rest time is at least about 1 second.

18. An absorbent article for absorbing liquid discharges of a wearer when worn in the crotch region of the wearer, the absorbent article comprising:
    first and second electrically conductive paths that are electrically isolated from one another and which are disposed about a periphery of the absorbent article such that a liquid discharge of the wearer that spreads to being between the first and second conductive paths provides a conductive path therebetween, which enables leak detection to be carried out, and
    a control unit comprising a computer readable memory, an impedance measurement circuit, a processor, an accelerometer, and a battery,
        wherein the computer readable memory stores impedance measurements, accelerometer measurements, and/or a time of the impedance measurements and/or accelerometer measurements;
        wherein the processor is configured to:
            obtain impedance measurements from the impedance measurement circuit;
            store the impedance measurements in the memory;
            compare the obtained impedance measurements to a predetermined threshold; and
            determine that a leakage state of the absorbent article has been reached if the predetermined threshold has been breached, wherein the predetermined threshold is set to distinguish over conductivity between the first and second conductive paths as a result of electrical conduction through the skin of the wearer or through moisture from the skin of the wearer as compared to saturation as a result of liquid discharge leakage.

19. The absorbent article of claim 18, wherein the first and second conductive paths are positioned peripherally outside of an absorbent core of the absorbent article when the absorbent article is viewed in plan when laid out flat.

20. The absorbent article of claim 18, wherein the absorbent article has first and second side edges shaped to fit with the legs of a wearer and the first and second conductive paths are arranged along at least one of the side edges.

21. The absorbent article of claim 18, wherein the first and second conductive paths are positioned along a leg elastic portion on at least one side of the absorbent article.

22. A system comprising a control unit and the absorbent article of claim 18, wherein the control unit is configured to apply a potential between the first and second conductive paths and to measure the impedance between them to allow determination of whether liquid discharge has spread to a position between the first and second conductive paths.

23. A system, comprising:
    an absorbent article for absorbing liquid discharge of a wearer when the absorbent article is worn in the crotch region of the wearer, wherein the absorbent article comprises a plurality of liquid discharge sensors that detect liquid discharge on the basis of a change in electrical property when the absorbent article is wetted, wherein each discharge sensor comprises two conductive paths, and a control unit configured to subject the plurality of liquid discharge sensors to pulses of electrical energy in order to take measurements of the electrical property with each pulse, wherein the pulses are separated by a rest period that is longer in duration than the duration of a pulse, wherein each of the plurality of liquid discharge sensors is pulsed sequentially to determine the electrical property for each liquid discharge sensor.

24. The system of claim 23, wherein the control unit comprises a battery from which the pulsed electrical energy is drawn.

25. The system of claim 23, wherein the control unit is mounted to the absorbent article.

26. The system of claim 23, wherein the control unit comprises a hard memory device onto which the measured electrical property is stored.

27. The system of claim 26, wherein the control unit comprises a memory buffer and the control unit is configured to store a plurality of sequential electrical property measurements for a given liquid discharge sensor in the memory buffer, wherein the control unit is configured to transfer the plurality of sequential electrical property measurements to the hard memory.

28. The system of claim 27, wherein the storage of data in the memory buffer and in the hard memory is powered by the battery.

29. The system of claim 23, wherein the pulses of electrical energy are not generated until the control unit has been contacted with a contact portion of the liquid discharge sensor.

30. The system of claim 23, wherein at least one conductive path of each pair of conductive paths is shared by two of the plurality of liquid discharge sensors.

31. An absorbent article for absorbing liquid discharge of a wearer when the absorbent article is worn in the crotch region of a wearer, the absorbent article comprising a front sheet for transferring the liquid discharge into the absorbent article, a back sheet for preventing escape of the liquid discharge from the absorbent article and an absorbent core for absorbing the liquid discharge and captured between the front sheet and the back sheet, wherein the absorbent article comprises at least one liquid discharge detection sensor to detect a wetness condition of the absorbent article on the basis of an electrical property associated with the detection sensor and the absorbent article, wherein the absorbent core has a Hardy integrity of at least 5 thrusts.

32. The absorbent article of claim 31, wherein the liquid discharge detection sensor includes first and second electrically isolated conductive paths and is operable by passing electrical current between the first and second conductive paths through the absorbent core when the absorbent core is wet and to measure the electrical property from the electrical current so passed.

33. The absorbent article of claim 32, wherein the first and second conductive paths are embedded in the absorbent core.

34. A system that comprises an absorbent article and a control unit, wherein the absorbent article is for absorbing liquid discharge when worn on the crotch region of the body of a user, and wherein the absorbent article comprises a plurality of detection zones for detecting the liquid discharge, each detection zone provided by first and second electrically conductive paths that are electrically isolated from one another and arranged so that a liquid discharge between the first and second conductive paths allows electrical current to flow between the first and second conductive paths which is able to be detected to detect the presence of liquid discharge in the respective zone, wherein the plurality of zones are longitudinally distributed with respect to the absorbent article along an absorbent core of the absorbent article to allow the longitudinal extent of the discharge to be ascertained, wherein the first and second conductive paths are longitudinally spaced from one another, and wherein the first and second conductive paths are elongate, are connected to the control unit by respective first and second leads insulated from the absorbent core, and are laterally aligned, and wherein the control unit is configured to measure an electrical property between the first and second conductive paths to allow detection of when the liquid discharge is present between the first and second conductive paths and to do so for each of the plurality of detection zones.

\* \* \* \* \*